United States Patent
Jelley et al.

(10) Patent No.: US 6,949,549 B2
(45) Date of Patent: Sep. 27, 2005

(54) IMIDAZOLOPHTHALAZINE DERIVATIVES AS LIGANDS FOR GABA$_A$ RECEPTORS

(75) Inventors: Richard Alexander Jelley, Sawbridgeworth (GB); Tamara Ladduwahetty, London (GB); Angus Murray MacLeod, Bishops Stortford (GB); Andrew Madin, Sawbridgeworth (GB); Francine Sternfeld, London (GB)

(73) Assignee: Merck Sharp & Dohme Ltd., Hoddesdon (GB)

(*) Notice: Subject to any disclaimer, the term of this patent is extended or adjusted under 35 U.S.C. 154(b) by 130 days.

(21) Appl. No.: 10/333,151

(22) PCT Filed: Jul. 13, 2001

(86) PCT No.: PCT/GB01/03170

§ 371 (c)(1),
(2), (4) Date: Jan. 16, 2003

(87) PCT Pub. No.: WO02/06285

PCT Pub. Date: Jan. 24, 2002

(65) Prior Publication Data

US 2004/0147517 A1 Jul. 29, 2004

(30) Foreign Application Priority Data

Jul. 17, 2000 (GB) .............................................. 0017518

(51) Int. Cl.[7] .................. A61K 31/5025; C07D 487/04
(52) U.S. Cl. ....................................... 514/248; 544/234
(58) Field of Search ........................... 544/234; 514/248

(56) References Cited

U.S. PATENT DOCUMENTS 6,528,649 B2 * 3/2003 Cai et al. ....................... 546/84

FOREIGN PATENT DOCUMENTS

| WO | WO 94 22865 A | 10/1994 |
| WO | WO 98 04559 A | 2/1998 |
| WO | WO 98 37648 A | 7/1999 |

OTHER PUBLICATIONS

Maubach, Medline Abstract for Current Drug Targets–CNS & Neurological Disorders, vol. 2,p. 233–239 (2003).*

X. Zhao, R. Zhang: Synth. Commun., vol. 25, 20, 1995, pp. 3271–3286, XP001033825.

* cited by examiner

*Primary Examiner*—Emily Bernhardt
(74) *Attorney, Agent, or Firm*—John C. Todaro; Melvin Winokur

(57) ABSTRACT

A class of substituted imidazolo[5,1-a]phthalazine derivatives as ligands for GABA$_A$ receptors of formula I

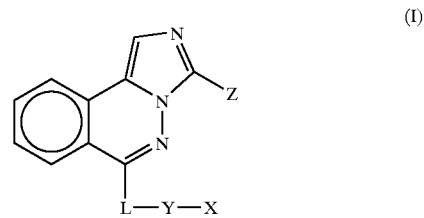

which are partial or full inverse agonists of an α5 receptor subunit while being relatively free of activity at α1 and/or α2 and/or α3 receptor subunit binding sites are described herein; they are therefore of benefit as a medicament for enhancing cognition but with the reduction or elimination of proconvulsant activity.

6 Claims, No Drawings

IMIDAZOLOPHTHALAZINE DERIVATIVES AS LIGANDS FOR GABA$_A$ RECEPTORS

CROSS REFERENCE TO RELATED APPLICATIONS

This application is a U.S. National Phase application under 35 U.S.C. § 371 of PCT Application No. PCT/GB01/03170, filed Jul. 13, 2001, which claims priority under 35 U.S.C. § 119 from GB Application No. 0017518.2, filed Jul. 17, 2000.

The present invention relates to a class of substituted imidazolophthalazine derivatives and to their use in therapy. More particularly, this invention is concerned with substituted imidazolo[5,1-a]phthalazine derivatives which are ligands for GABA$_A$ receptors containing the α5 subunit and are therefore useful in therapy where cognition enhancement is required.

Receptors for the major inhibitory neurotransmitter, gamma-aminobutyric acid (GABA), are divided into two main classes: (1) GABA$_A$ receptors, which are members of the ligand-gated ion channel superfamily; and (2) GABA$_B$ receptors, which may be members of the G-protein linked receptor superfamily. Since the first cDNAs encoding individual GABA$_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the GABA$_A$ receptor gene family represents a huge step forward in our understanding of this ligand-gated ion channel, insight into the extent of subtype diversity is still at an early stage. It has been indicated that an α subunit, β subunit and a γ subunit constitute the minimum requirement for forming a fully functional GABA$_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native GABA$_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of GABA$_A$ receptors in the rat. Subtype assemblies containing α2 and α3 subunits respectively account for about 25% and 17% of GABA$_A$ receptors in the rat. Subtype assemblies containing an α5 subunit are primarily hippocampal and represent about 4% of receptors in the rat.

A characteristic property of some GABA$_A$ receptors is the presence of a number of modulatory sites, of which the most explored is the benzodiazepine (BZ) binding site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radioligand binding studies. The BZ1 subtype has been shown to be pharmacologically equivalent to a GABA$_A$ receptor comprising the α1 subunit in combination with β2 and γ2. This is the most abundant GABA$_A$ receptor subtype, representing almost half of all GABA$_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist β-CCM enhanced spatial learning in the Morris watermaze. However, β-CCM and other conventional benzodiazepine receptor inverse agonists are proconvulsant which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or fill inverse agonists.

It has now been discovered that use of an α5 receptor partial or full inverse agonist which is relatively free of activity at α1 and/or α2 and/or α3 receptor binding sites can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

The present invention provides a compound of formula I, or a pharmaceutically acceptable salt thereof:

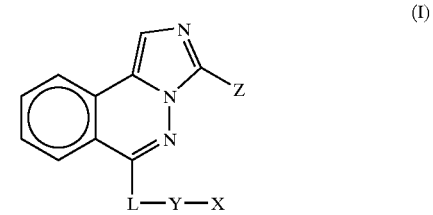

(I)

wherein

L is O, S or NR$^n$ where R$^n$ is H, C$_{1-6}$alkyl or C$_{3-6}$cycloalkyl;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene or pyridine ring and the heteroaromatic ring being optionally substituted by R$^x$ and/or R$^y$ and/or R$^z$, where R$^x$ is halogen, R$^3$, OR$^3$, OCOR$^3$, NR$^4$R$^5$, NR$^4$COR$^5$, OH, tri(C$_{1-6}$alkyl)silylC$_{1-6}$alkoxyC$_{1-4}$alkyl, CN or R$^6$, R$^y$ is halogen, R$^3$, OR$^3$, OCOR$^3$, NR$^4$R$^5$, NR$^4$COR$^5$, NR$^4$R$^5$(C$_{1-6}$)alkyl or CN and R$^z$ is R$^3$, OR$^3$ or OCOR$^3$, providing that when X is a pyridine derivative, the pyridine ring is optionally in the form of the N-oxide, and providing that when X is a tetrazole derivative it is protected by a C$_{1-4}$alkyl group;

Y is optionally branched C$_{1-4}$alkylene optionally substituted by an oxo group or Y is a group (CH$_2$)$_j$O wherein the oxygen atom is nearest the group X and j is 2, 3 or 4;

Z represents a phenyl ring, a 5-membered heteroaromatic ring containing 1, 2 or 3 heteroatoms independently selected from oxygen, nitrogen and sulphur, at most one of the heteroatoms being oxygen or sulphur, or a 6-membered heteroaromatic ring containing 1, 2 or 3 nitrogen atoms with the exception of pyrazine, any of which rings may be optionally substituted with one or more substituents selected from halogen, $R^3$, $OR^3$, $OCOR^3$, $NR^4R^5$, $NR^4R^5(C_{1-6})$alkyl, $NR^4R^5CO$, $NR^4R^5CO(C_{1-6})$alkyl, CN, cyano$(C_{1-6})$alkyl or $R^6$;

$R^3$ represents $C_{1-6}$alkyl, $C_{2-6}$alkenyl, $C_{2-6}$alkyl, $C_{3-6}$cycloalkyl, $C_{3-6}$cycloalkyl$(C_{1-6})$alkyl, cyano$(C_{1-6})$alkyl, hydroxy$C_{1-6}$alkyl and $R^3$ is optionally mono, di- or tri-fluorinated;

$R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with a nitrogen atom to which they are commonly attached, form a 4–7 membered heteroaliphatic ring containing the said nitrogen atom and optionally one other heteroatom selected from O, N and S; and $R^6$ is $C_{6-10}$aryl, $C_{6-10}$aryl $(C_{1-6})$alkyl, heteroaryl or heteroaryl$(C_{1-6})$alkyl, where heteroaryl is a five-membered aromatic ring containing one, two, three or four nitrogen atoms or one oxygen atom or sulphur atom and optionally one or two nitrogen atoms or a six-membered aromatic ring containing one, two or three nitrogen atoms, and $R^6$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

The expression "$C_{3-6}$cycloalkyl" as used herein includes cyclic propyl, butyl, pentyl and hexyl groups such as cyclopropyl and cyclohexyl.

The expression "$C_{3-6}$ cycloalkyl$(C_{1-6})$alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

The expression "$C_{1-4}$alkylene" as used herein refers to alkanediyl groups of up to 4 carbon atoms in which the unsatisfied valencies reside on the same carbon atom or on different carbon atoms.

Typical $C_{6-8}$ bicycloalkyl groups include bicyclo[2.1.1]hexyl and bicyclo[2.2.1]heptyl.

Typical aryl groups include phenyl and naphthyl, preferably phenyl.

The expression "aryl$(C_{1-6})$alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Unless otherwise specified, 5- and 6-membered heteroaromatic rings shall include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine. When a heteroaromatic ring comprises a hydroxy group as a substituent, and keto-enol tautomerism is possible, both tautomers are included within the scope of the invention. Thus, for example, a 3-hydroxy-1,2,4-triazole ring will be considered equivalent to the 3-keto tautomer.

The expression "heteroaryl$(C_{1-6})$alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy, butoxy, pentoxy and hexoxy groups, including cyclopropylmethoxy. Derived expressions such as "$C_{2-6}$alkenyloxy", "$C_{2-6}$alkynyloxy", "$C_{1-4}$alkoxy", "$C_{2-4}$alkenyloxy" and "$C_{2-4}$alkyloxy" should be construed in an analogous manner.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Preferably L is an oxygen atom. L may also be S or $NR''$ in which $R''$ is preferably hydrogen or methyl. $R''$ may be hydrogen.

X is generally: pyridyl, pyrazinyl, pyridazinyl or pyrimidinyl optionally substituted by a halogen atom or a group $R^3$, $OR^3$, $NR^4R^5$ or a five membered heteroaromatic ring containing 1, 2 or 3 nitrogen atoms, and X is optionally fused to a benzene ring; a 5-membered heteroaromatic ring containing 2 or 3 heteroatoms chosen from oxygen, sulphur and nitrogen, at most one of the heteroatoms being oxygen or sulphur, which is unsubstituted or substituted by one, two or three groups independently chosen from halogen and $R^3$, or which is substituted by a pyridyl, phenyl or benzyl ring which ring is optionally independently substituted by one, two or three halogen atoms or $C_{1-6}$alkyl or $CF_3$ groups; or phenyl optionally substituted by one, two or three independently chosen halogen atoms.

Alternatively, X may represent a 5-membered heteroaromatic ring containing 2 or 3 heteroatoms chosen from oxygen, sulphur and nitrogen, at most one of the heteroatoms being oxygen or sulphur, which is fused to a benzene or pyridine ring, or which is substituted by $NH_2$ or by OH which may exist as the keto tautomer; or X may represent a tetrazole ring bearing a $C_{1-4}$alkyl substituent.

When X is a substituted 6-membered heteroaromatic ring: $R^x$ is preferably halogen, $R^3$, $OR^3$, $NR^4R^5$ or a five-membered heteroaromatic ring containing 1, 2 or 3 nitrogen atoms and more preferably methyl, $CF_3$, methoxy, bromine, chlorine, isopropoxy, dimethylamino or a five-membered heterocyclic ring containing 1, 2 or 3 nitrogen atoms; and $R^y$ and $R^z$ are preferably absent.

When X is a substituted 5-membered heteroaromatic ring: $R^x$ is preferably halogen, $R^3$ or a pyridyl, phenyl or benzyl ring, which ring is optionally independently substituted by one, two or three halogen atoms or $C_{1-6}$alkyl or $CF_3$ groups, and more preferably $R^x$ is methyl, $CF_3$, chlorine or a phenyl, pyridyl or benzyl ring which ring is unsubstituted or substituted by chlorine or $CF_3$; and $R^y$ and $R^z$ are preferably halogen or $R^3$ or are absent, and more preferably are methyl, $CF_3$ or chlorine, or are absent.

X is preferably a substituted triazolyl, such as 2-methyl-1,2,4-triazol-5yl.

X is preferably pyridyl or substituted pyridyl, such as pyrid-2-yl and 3-methoxypyrid-2-yl.

Apt values for Y include $CH_2$, $CH(CH_3)$, $CH_2CH_2$ and $CH_2CH_2CH_2$ optionally substituted by an oxo group, and $CH_2CH_2O$ and $CH_2CH_2CH_2O$. For example, Y can be $CH_2$, $CH_2CH_2$, $CH_2CH_2CH_2$, $CH_2CH_2O$ or $CH_2CH_2CH_2O$. Preferably Y is $CH_2$ or $CH_2CH_2$ and most preferably $CH_2$.

From the foregoing it will be understood that particularly suitable groups L-Y—X are $OCH_2X$ groups where X is pyridyl or substituted pyridyl.

Suitable values for Z include optionally substituted phenyl, pyrimidinyl, triazinyl, pyrrolyl, oxazolyl, isoxazolyl, thiazolyl, isothiazolyl, oxadiazolyl and thiadiazolyl groups.

Z is very aptly an optionally substituted 5-membered heteroaromatic ring containing one oxygen and one or two nitrogen ring atoms.

Favoured values for Z include optionally substituted phenyls and isoxazoles.

Typical substituents on Z include $C_{1-6}$alkyl, $C_{3-6}$cycloalkyl, hydroxy$C_{1-6}$alkyl, pyridyl, thienyl or amino, particularly methyl, ethyl, isopropyl, cyclopropyl, thienyl or pyridyl.

Z may be unsubstituted.

Z may very aptly be substituted by methyl.

Particular values of Z include 5-methylisoxazol-3-yl and phenyl. Z may also be isoxazol-3-yl.

A particular sub-class of compounds according to the invention is represented by the compounds of formula IIA, and pharmaceutically acceptable salts thereof.

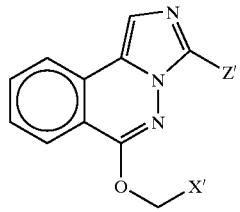

(IIA)

wherein
X' represents, pyrazolyl, isoxazolyl, thiazolyl, imidazolyl, thiadiazolyl, benzimidazolyl, oxadiazolyl, triazolyl, tetrazolyl, pyridinyl, pyridazinyl, oxazolopyridinyl, pyrimidinyl, pyrazinyl, quinolinyl, isoquinolinyl or quinoxalinyl, any of which groups may be optionally substituted by one or more of $C_{1-6}$ alkyl, amino, pyridyl, $CF_3$, aryl($C_{1-6}$)alkyl, pyridyl($C_{1-6}$)alkyl, halogen, cyano, cyano ($C_{1-6}$)alkyl, hydroxymethyl, $C_{1-6}$alkoxy, $C_{3-6}$cycloalkyl ($C_{1-6}$)alkoxy, hydroxy or the keto tautomer thereof, di($C_{1-6}$)alkylamino($C_{1-6}$)alkyl, amino($C_{1-6}$)alkyl, N-($C_{1-6}$) alkylpiperidinyl, pyrrolidinyl($C_{1-6}$)alkyl, piperazinyl($C_{1-6}$) alkyl and morpholinyl($C_{1-6}$)alkyl; and Z' represents a phenyl ring or a 5-membered heteroaromatic ring containing one oxygen and one or two nitrogen ring atoms each of which rings is optionally substituted with $C_{1-6}$alkyl or $C_{1-6}$alkoxy.

Particular compounds within the scope of the present invention include:
6-(2-pyridy)methyloxy-3-phenylimidazo[5,1-a]phthalazine;
6-(3-methoxypyridin-2-yl)methyloxy-3-(5-methylisoxazol-3-yl)imidazo[5,1-a]phthalazine;
and pharmaceutically acceptable salts thereof.

The compounds of the present invention have a good binding affinity (Ki) for the α5 subunit of the $GABA_A$ receptor. In a preferred embodiment the compounds of the invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment of the human body. Preferably the treatment is for a condition associated with $GABA_A$ receptors comprising the α5 subunit and/or for the enhancement of cognition. Preferably the condition is a neurological deficit with an associated cognitive disorder such as a dementing illness such as Alzheimer's disease. Other conditions to be treated include cognition deficits due to traumatic injury, stroke, Parkinson's disease, Downs syndrome, age related memory deficits, attention deficit disorder and the like.

The present invention further provides the use of a compound of the present invention in the manufacture of a medicament for the enhancement of cognition, preferably in a human suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

Thus, the compounds of the present invention can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For the enhancement of cognition, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

There is also provided a process for producing a compound of formula I which comprises reacting a compound of formula II with a compound of formula III:

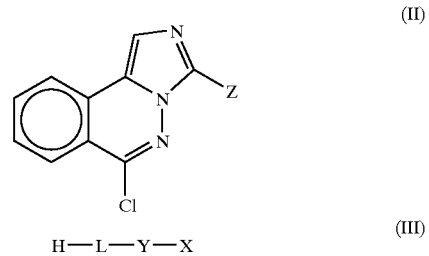

H—L—Y—X (III)

wherein L, X, Y and Z are as defined above, generally in the presence of a base such as sodium hydride or lithium bis(trimethylsilyl)amide, and a solvent such as a mixture of tetrahydrofuran and N,N-dimethylformamide at a temperature of between −78° C. and room temperature.

The compounds of formula II can be made by reacting a compound of formula IV with a chlorinating agent such as $POCl_3$:

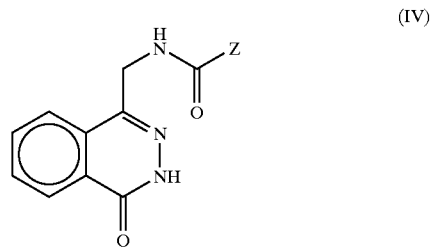

wherein Z is as defined above, generally at elevated temperature, such as from 85–120° C., for about 0.5 to 2.5 hours, optionally followed by heating at reflux with a catalyst such as $Et_3N.HCl$ in a solvent such as xylene.

The compounds of formula IV can be produced by reacting a compound of formula V with 4-aminomethyl-2H-phthalazin-1-one hydrochloride (Geterotsikl. Soedin., 1972, (9), 15):

wherein Z is as defined above generally in the presence of a base such as triethylamine and a solvent such as dimethylformamide.

Compounds of formulae III and V are commercially available or can be made from commercially available compounds by known methods.

It will be understood that any compound of formula I initially obtained from any of the above processes may, where appropriate, subsequently be elaborated into a further compound of formula I by techniques known from the art.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The compounds in accordance with this invention potently inhibit the binding of [3H]-flumazenil to the benzodiazepine binding site of human $GABA_A$ receptors containing the $\alpha 5$ subunit stably expressed in Ltk-cells.

Reagents

Phosphate buffered saline (PBS).

Assay buffer: 10 mM $KH_2PO_4$, 100 mM KCl, pH 7.4 at room temperature.

[3H]-Flumazenil (18 nM for $\alpha 1\beta 3\gamma 2$ cells; 18 nM for $\alpha 2\beta 3\gamma 2$ cells; 10 nM for $\alpha 3\beta 3\gamma 2$ cells; 10 nM for $\alpha 5\beta 3\gamma 2$ cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [3H]-flumazenil (final concentration for $\alpha 1\beta 3\gamma 2$: 1.8 nM; for $\alpha 2\beta 3\gamma 2$: 1.8 nM; for $\alpha 3\beta 3\gamma 2$: 1.0 nM; for $\alpha 5\beta 3\gamma 2$: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant Ki can be calculated for each test compound.

The compounds of the accompanying Examples were tested in the above assay, and all were found to possess a Ki value for displacement of [3H]Ro 15-1788 from the $\alpha 5$ subunit of the human $GABA_A$ receptor of 100 nM or less, most were at 50 nM or less, many were at 10 nM or less and some were at 1 nM or less.

The compounds of the present invention have been shown to enhance cognition in the rat water maze test (Morris, Learning and Motivation, 1981, 12, 239ff). Further details of methodology for demonstrating that the present compounds enhance cognition can be found in WO-A-9625948.

The following Examples illustrate the present invention:

EXAMPLE 1

6-(2-Pyridyl)methyloxy-3-phenylimidazo[5,1-a] phthalazine a) N-(4-Oxo-3,4-dihydrophthalazin-1-ylmethyl)benzamide Triethylamine (5.9 ml, 42 mmol) was added dropwise to a stirred suspension of 4-aminomethyl-2H-phthalazin-1-one hydrochloride (Geterotsikl. Soedin, 1972, (9), 15) (3.00 g, 14.2 mmol) in DMF (150 ml) at room temperature under nitrogen. The mixture was stirred for 1.5 h before the addition of benzoyl chloride (2.5 ml, 22 mmol) and then stirred at room temperature overnight. The reaction mixture was filtered and water added to the filtrate to form a solid. The mixture was cooled and the solid collected by filtration, washed successively with diethyl ether and isohexane, and dried in vacuo to give the title-compound (3.18 g, 80%), $^1$H NMR (360 MHZ, $d^6$-DMSO) δ 4.81 (2H, d, J=5.6 Hz, $CH_2$), 7.43–7.53 (3H, m, 3 of Ar—H), 7.83–7.96 (4H, m, 4 of Ar—H), 8.08 (1H, d, J=7.9 Hz, Ar—H), 8.28 (1H, dd, J=7.8 and 1.2 Hz, Ar—H), 8.98 (1H, br s, NH), 12.62 (1H, s NH).

b) 6-Chloro-3-phenylimidazo[5,1-a]phthalazine

A suspension of the preceding product (2.48 g, 8.88 mmol) in phosphorus oxychloride (118 ml) was heated at reflux under nitrogen for 2.5 h. The solvent was evaporated in vacuo and the residue azeotroped with toluene, diluted with dichloromethane and water and the mixture basified with solid sodium carbonate. The layers were separated and the aqueous layer was extracted with dichloromethane (×2). The combined organic layers were dried ($MgSO_4$) and evaporated in vacuo and the residue purified by chromatography on silica gel, eluting with 1→3% methanol/dichloromethane (gradient elution), to give the title-compound (1.00 g, 40%), $^1$H NMR (360 MHz, $CDCl_3$) δ 7.41–7.59 (4H, m, 4 of Ar—H), 7.79 (1H, t, J=7.6 Hz, Ar—H), 7.88 (1H, s, Ar—H), 8.02 (1H, d, J=7.7 Hz, Ar—H), 8.12 (1H, m, Ar—H), 8.39–8.41 (2H, m, 2 of Ar—H).

c) 6-(2-Pyridyl)methyloxy-3-phenylimidazo[5,1-a] phthalazine

Sodium hydride (30 mg of a 60% dispersion, 0.75 mmol) was added to a stirred solution of the preceding product (116 mg, 0.41 mmol) and 2-pyridylcarbinol (0.080 ml, 0.83 mmol) in DMF (5 ml) at room temperature under nitrogen. After 1.5 h, water was added and the mixture was evaporated in vacuo. The residue was partitioned between dichloromethane and water and the aqueous layer was separated and further extracted with dichloromethane (×2). The combined organic extracts were dried (Na$_2$SO$_4$) and evaporated in vacuo and the residue purified by chromatography on silica gel, eluting with 20% ethyl acetate/dichloromethane, followed by recrystallisation (ethyl acetate/hexane) to give the title-product (70 mg, 48%), $^1$H NMR (250 MHz, CDCl$_3$) δ 5.70 (2H, s, CH$_2$), 7.30–7.59 (6H, m, 6 of Ar—H), 7.72–7.76 (2H, m, 2 of Ar—H), 7.82 (1H, s, Ar—H), 7.99 (1H, d, J=7.9 Hz, Ar—H), 8.18 (1H, d, J=8.0 Hz, Ar—H), 8.29–8.34 (2H, m, 2 of Ar—H), 8.70 (1H, br d, Ar—H); MS (ES$^+$) m/e 353 [MH]$^+$.

EXAMPLE 2

6-(3-Methoxypyridin-2-yl)methyloxy-3-(5-methylisoxazol-3-yl)imidazo[5,1-a]phthalazine a) 5-Methylisoxazole-3-carboxylic acid (4-oxo-3,4-dihydroiohthalazin-1-ylmethyl)amide The title compound was prepared from 4-aminomethyl-2H-phthalazine-1-one hydrochloride (Geterotsikl. Soedin, 1972, (9), 15) and 5-methylisoxazole-3-carbonyl chloride using the procedure described in Example 1, Part a). $^1$H NMR (360 MHz, d$^6$-DMSO) δ 2.45 (3H, d, J=0.6 Hz, CH$_3$), 4.77 (2H, d, J=5.8 Hz, CH$_2$), 6.57 (1H, d, J=0.7 Hz, Ar—H), 7.86 (1H, t, J=8.2 Hz, Ar—H), 7.94 (1H, t, J=8.1 Hz, Ar—H), 8.06 (1H, d, J=7.6 Hz, Ar—H), 8.28 (1H, d, J=8.0 Hz, Ar—H), 9.12 (1H, t, J=5.7 Hz, NH) and 12.61 (1H, S, NH).

b) 6-Chloro-3-(5-methylisoxazol-3-yl)-imidazo[5,1-a]phthalazine

The amide (3.2 g, 0.011 mol) was dissolved in phosphorus oxychloride (120 ml) and heated at 90° C. for 0.5 h under nitrogen. The solvent was removed in vacuo and the residue azeotroped with toluene (2×). The resulting brown oil was dissolved in xylene (120 ml) and heated at reflux for 1 h. The solvent was removed in vacuo and the residue purified by chromatography on silica gel, eluting with 2% methanol/dichloromethane. Further chromatographic purification eluting with 20% ethyl acetate/dichloromethane gave the title-compound as a yellow solid (0.65 g, 20%), $^1$H NMR (360 MHz, CDCl$_3$) δ 2.55 (3H, d, J=0.8 Hz, CH$_3$), 6.87 (1H, d, J=0.7 Hz, Ar—H), 7.64 (1H, t, J=7.4 H$_2$, Ar—H), 7.85 (1H, t, J=7.4 Hz, Ar—H), 7.95 (1H, s, Ar—H), 8.06 (1H, d, J=8.1 Hz, Ar—H), 8.18 (1H, d, J=8.1 Hz, Ar—H); MS (ES$^+$) m/e 284 [MH]$^+$.

c) (3-Methoxypyridin-2-yl)methanol

Dimethylsulphoxide (15 ml) was added to ground potassium hydroxide (10.2 g, 0.186 mol) and stirred for 0.25 h at room temperature under nitrogen. 3-Hydroxy-(2 hydroxymethyl)pyridine hydrochloride (5.0 g, 0.031 mol) in dimethylsulphoxide (20 ml) was added via syringe. After stirring for 1 h, methyl iodide (1.92 ml, 0.031 mol) was added and the reaction stirred at room temperature overnight. Water (100 ml) was added and the mixture acidified to pH1 with 5N hydrochloric acid. The aqueous layer was washed with dichloromethane (×3), basified to pH14 with sodium hydroxide and extracted with dichloromethane (×4). The combined organic extracts were dried (MgSO$_4$), the solvent removed in vacuo and the residue purified by chromatography eluting with dichloromethane/methanol/ammonia (90:5:0.5), to give the title-compound, $^1$H NMR (360 MHz, CDCl$_3$) δ 3.86 (3H, d, J=1.8 Hz, CH$_3$), 4.29 ($^1$H, t, J=4.5 Hz, OH), 4.74 (2H, d, J=4.1 Hz, CH$_2$), 7.12–7.22 (2H, m, 2 of Ar—H) and 8.15 (1H, d, J=4.7 Hz, Ar—H).

d) 6-(3-Methoxypyridin-2-yl)methyloxy-3-(5-methylisoxazol-3-yl)imidazo[5,1-a]phthalazine To the preceding alcohol (52 mg, 0.38 mmol) dissolved in N,N-dimethylformamide (1 ml) and tetrahydrofuran (2.5 ml) was added the product of part b above (100 mg, 0.35 mmol) and the mixture stirred at −78° C. under nitrogen for 0.5 h. Lithium bis(trimethylsilyl)amide (0.42 ml of 1.0 M solution in hexanes, 0.42 mmol) was added and the reaction allowed to warm up gradually to room temperature overnight. The reaction mixture was then heated at 50° C. for 5 h. The solvent was removed in vacuo and the residue azeotroped with xylene (×2) and purified by chromatography on silica gel, eluting with 0→5% methanol/dichloromethane, followed by recrystallisation (dichloromethane/hexane) to give the title-compound (41 mg, 32%) as a pale yellow solid, $^1$H NMR (360 MHz, CDCl$_3$) δ 2.52 (3H, s, CH$_3$), 3.89 (3H, s, CH$_3$), 5.75 (2H, s, CH$_2$), 6.87 (1H, s, Ar—H), 7.26–7.34 (2H, m, 2 of Ar—H), 7.48 (1H, t, J=7.3 Hz, Ar—H), 7.74 (1H, t, J=7.3 Hz, Ar—H), 7.86 (1H, d, J=0.6 Hz, Ar—H), 8.00 (1H, d, J=8.1 Hz, Ar—H), 8.13 (1H, d, J=8.1 Hz, Ar—H), 8.25 (1H, d, J=4.4 Hz, Ar—H); MS (ES$^+$) m/e 388 [MH]$^+$.

EXAMPLE 3

6-(2-Methyl-1,2,4-triazol-5-yl)methyloxy-3-(isoxazol-3-yl)imidazo[5,1-a]phthalazine a) Isoxazol-3-carboxylic acid (4-oxo-3,4-dihydrophthalazin-1-ylmethyl)amide The title compound was prepared from 4-aminomethyl-2H-phthalazine-1-one hydrochloride (Geterotsikl, Soedin, 1972, (9), 15) and isoxazol-3-carbonyl chloride using the procedure described in Example 1, Part a. $^1$H NMR (360 MHz, d$^6$-DMSO) δ 4.80 (d, J=6 Hz, 2H), 6.93 (s, 1H), 7.87 (t, J=7 Hz, 1H), 7.95 (t, J=7 Hz, 1H), 8.1 (d, J=7 Hz, 1H), 8.28 (dd, J=2 Hz, 7 Hz, 1H), 9.08 (s, 1H), 9.09 (t, J=2 Hz, 1H), 12.62 (s, 1H).

b) 6-Chloro-3-(isoxazol-3-yl)-imidazo[5,1-a]phthalazine

The title compound was prepared from isoxazol-3-carboxylic acid (4-oxo-3,4-dihydrophthalazin-1-ylmethyl) amide (Part a) and phosphorus oxychloride according the procedure described in Example 1, Part b. $^1$H NMR (360 MHz, CDCl$_3$) δ 7.25 (s, 1H), 7.66 (t, J=8 Hz, 1H), 7.86 (t, J=8 Hz, 1H), 7.97 (brs, 1H), 8.09 (d, J=8 Hz, 1H), 8.21 (d, J=8 Hz, 1H), 8.57 (d, J=2 Hz, 1H).

c) 6-(2-Methyl-1,2,4-triazol-5-yl)methyloxy-3-(isoxazol-3-yl)imidazo[5,1-a]phthalazine The title compound was prepared from 6-chloro-3-(isoxazol-3-yl)-imidazo[5,1-a]phthalazine (Part b) and (2-methyl-1,2,4-triazol-5-yl)methanol as described in Example 1, Part c. $^1$H NMR (360 MHz, CDCl$_3$) δ 3.96 (s, 3H), 5.7 (s, 2H), 7.40 (s, 1H), 7.52 (t, J=8 Hz, 1H), 7.76 (t, J=8 Hz, 1H), 7.89 (s, 1H), 8.0 (d, J=8 Hz, 1H), 8.17 (d, J=8 Hz, 1H), 8.56 (s, 1H). MS (ES$^+$) m/e 348 [MH]$^+$.

What is claimed is:

1. A compound of formula I, or a pharmaceutically acceptable salt thereof:

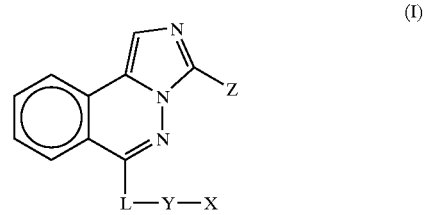

(I)

wherein

L is O, S or NR" where R" is H, $C_{1-6}$alkyl or $C_{3-6}$cycloalkyl;

X is a pyridyl or 1,2,4-triazolyl ring, which is optionally substituted by $R^x$ and/or $R^y$ and/or $R^z$, where $R^x$ is halogen, $R^3$, $OR^3$, $OCOR^3$, $NR^4R^5$, $NR^4COR^5$, OH, tri($C_{1-6}$alkyl)silyl$C_{1-6}$alkoxy$C_{1-4}$alkyl, CN or $R^6$, $R^y$ is halogen, $R^3$, $OR^3$, $OCOR^3$, $NR^4R^5$, $NR^4COR^5$, $NR^4R^5$($C_{1-6}$)alkyl or CN and $R^z$ is $R^3$, $OR^3$ or $OCOR^3$, providing that when X is a pyridine derivative, the pyridine ring is optionally in the form of the N-oxide;

Y is optionally branched $C_{1-4}$alkylene optionally substituted by an oxo group or Y is a group $(CH_2)_jO$ wherein the oxygen atom is nearest the group X and j is 2, 3 or 4;

Z represents a isoxazolyl ring which may be optionally substituted with one or more substituents selected from halogen, $R^3$, $OR^3$, $OCOR^3$, $NR^4R^5$, $NR^4R^5(C_{1-6})$alkyl, $NR^4R^5CO$, $NR^4R^5CO(C_{1-6})$alkyl, CN, cyano($C_{1-6}$)alkyl or $R^6$;

$R^3$ represents $C_{1-6}$alkyl, $C_{2-6}$alkenyl, $C_{2-6}$alkynyl, $C_{3-6}$cycloalkyl, $C_{3-6}$cycloalkyl($C_{1-6}$)alkyl, cyano($C_{1-6}$)alkyl, hydroxy$C_{1-6}$alkyl and $R^3$ is optionally mono-, di- or tri-fluorinated;

$R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with a nitrogen atom to which they are commonly attached, form a 4–7 membered heteroaliphatic ring containing the said nitrogen atom and optionally one other heteroatom selected from O, N and S; and $R^6$ is $C_{6-10}$aryl, $C_{6-10}$aryl ($C_{1-6}$)alkyl, heteroaryl or heteroaryl($C_{1-6}$)alkyl, where heteroaryl is a five-membered aromatic ring containing one, two, three or four nitrogen atoms or one oxygen atom or sulphur atom and optionally one or two nitrogen atoms or a six-membered aromatic ring containing one, two or three nitrogen atoms, and $R^6$ is optionally substituted by one, two or three substituents independently chosen from halogen atoms and $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms.

2. A compound as claimed in claim 1 represented by a compound of formula IIA, or a pharmaceutically acceptable salt thereof:

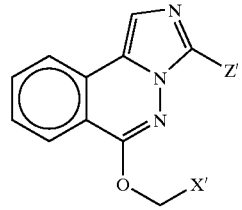

(IIA)

wherein

X' represents 1,2,4-triazolyl or pyridinyl, which may be optionally substituted by one or more of $C_{1-6}$ alkyl, amino, pyridyl, $CF_3$, aryl($C_{1-6}$)alkyl, pyridyl($C_{1-6}$)alkyl, halogen, cyano, cyano($C_{1-6}$)alkyl, hydroxymethyl, $C_{1-6}$alkoxy, $C_{3-6}$cycloalkyl($C_{1-6}$) alkoxy, hydroxy or the keto tautomer thereof, di($C_{1-6}$) alkylamino($C_{1-6}$)alkyl, amino($C_{1-6}$)alkyl, N-($C_{1-6}$) alkylpiperidinyl, pyrrolidinyl($C_{1-6}$)alkyl, piperazinyl ($C_{1-6}$)alkyl and morpholinyl($C_{1-6}$)alkyl; and Z' represents an isoxazoly ring which is optionally substituted with $C_{1-6}$alkyl or $C_{1-6}$alkoxy.

3. A compound selected from: 6-(3-methoxypyridin-2-yl) methyloxy-3-(5-methylisoxazol-3-yl)imidazo[5,1 -a]phthalazine; 6-(2-Methyl- 1,2,4-triazol-5-yl)methyloxy-3-(isoxazol-3-yl)imidazo[5,1 -a]phthalazine; and pharmaceutically acceptable salts thereof.

4. A process for the preparation of a compound as claimed in claim 1 which comprises reacting a compound of formula II with a compound of formula III:

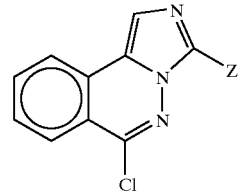

(II)

H—L—Y—X  (III)

wherein L, X, Y and Z are as defined in claim 1.

5. A method of enhancing cognition of a subject suffering from Alzheimer's Disease which comprises administering to that subject an effective amount of a compound of formula I as defined in claim 1, or a pharmaceutically acceptable salt thereof.

6. A pharmaceutical composition comprising a compound of claim 1 or a pharmaceutically acceptable salt thereof and a pharmaceutically acceptable carrier.

* * * * *